United States Patent [19]
Smith et al.

[11] Patent Number: 5,120,469
[45] Date of Patent: Jun. 9, 1992

[54] AMINE OXIDE COMPOSITION AND PROCESS

[75] Inventors: Kim R. Smith; James E. Borland; Joe D. Sauer, all of Baton Rouge, La.

[73] Assignee: Ethyl Corporation, Richmond, Va.

[21] Appl. No.: 524,569

[22] Filed: May 17, 1990

[51] Int. Cl.$^5$ .................. B01F 17/16; C07C 283/04; C11D 3/30
[52] U.S. Cl. .................. 252/357; 252/547; 252/DIG. 14; 564/298
[58] Field of Search ............... 252/357, 547, DIG. 14; 564/298

[56] References Cited

U.S. PATENT DOCUMENTS

| | | | |
|---|---|---|---|
| 2,169,976 | 8/1939 | Guenther et al. | 252/357 X |
| 3,410,903 | 11/1968 | Solomon | 252/547 X |
| 3,449,431 | 6/1969 | Swenson | 252/547 X |
| 3,565,810 | 2/1971 | Mausner et al. | 252/547 |
| 3,914,185 | 10/1975 | Inamorato | 252/547 X |
| 4,247,424 | 1/1981 | Kuzel et al. | 252/357 X |
| 4,264,479 | 4/1981 | Flanagan | 252/357 X |
| 4,276,205 | 6/1981 | Ferry | 252/547 X |
| 4,749,509 | 6/1988 | Kacher | 252/DIG. 14 |
| 5,055,232 | 10/1991 | Sauer et al. | 252/547 |
| 5,055,614 | 10/1991 | Sauer et al. | 564/297 X |

FOREIGN PATENT DOCUMENTS

| | | | |
|---|---|---|---|
| 0224662 | 6/1987 | European Pat. Off. | 564/298 |
| 0105495 | 6/1982 | Japan | 252/547 |

OTHER PUBLICATIONS

Kirk-Othmer, *Encyclopedia of Chemical Technology*, Third Ed., 1978, vol. 2, pp. 259-271.

*Primary Examiner*—Richard D. Lovering
*Attorney, Agent, or Firm*—Patricia J. Hogan

[57] ABSTRACT

A pourable amine oxide composition which is suitable for use in detergent compositions is obtained by reacting a tert-amine with aqueous hydrogen peroxide in a nonionic surfactant as the sole organic solvent, at least a portion of the nonionic surfactant being a fatty alcohol ethoxylate or other compound corresponding to the formula $Z[OC(Z')HCH_2]_mOH$ in which Z is an alkyl group containing 4-30 carbons, Z' is hydrogen or an alkyl or hydroxyalkyl group containing 1-3 carbons, and m is an integer of 1-100. When the composition has a low water content, it is suitable for use in water-sensitive formulations, such as bar soaps and detergent concentrates.

24 Claims, No Drawings

AMINE OXIDE COMPOSITION AND PROCESS

FIELD OF INVENTION

This invention relates to amine oxide compositions and more particularly to such compositions suitable for incorporation into water-sensitive detergent formulations and to processes for preparing them.

BACKGROUND

As disclosed in Kirk-Othmer, *Encyclopedia of Chemical Technology*, Third Edition, 19878, Volume 2, pp. 259–271, it is known that amine oxides which are useful in various applications, such as detergent and shampoo formulations, can be prepared by reacting non-heterocyclic tert-amines with aqueous hydrogen peroxide in a solvent such as water, a lower alcohol, acetone, or acetic acid.

Copending application Ser. No. 415,910 (Smith et al.), filed Oct. 2, 1989, not abandoned teaches that it is also possible to prepare the amine oxides as solid, non-hygroscopic dihydrates by conducting their syntheses in organic solvents, such as esters, hydrocarbons, and highly polar solvents, in which the products are soluble at reaction temperatures but insoluble at a lower temperature.

These amine oxides, which are generally trialkylamine oxides, particularly trialkylamine oxides containing both short and long alkyl groups, are sometimes utilizable as prepared. However, the solid amine oxides present handling problems; and the solvents used in the known syntheses of amine oxides, especially the flammable solvents and water, are apt to be undesirable in some applications. Moreover, even when not undesirable because of making a harmful contribution, such as an excess of water in a water-sensitive formulation, the solvents have the unattractive feature of contributing weight and bulk to amine oxide-containing formulations without serving a useful purpose therein.

It would be advantageous to be able to provide amine oxide compositions which could be poured or pumped from the vessels in which they are prepared to combine them with other ingredients of formulations in which they are to be incorporated, e.g., water-sensitive formulations, without having them in conjunction with solvents that would serve no useful function in the formulations and could be deleterious.

U.S. Pat. No. 3,565,810 (Mausner et al.) shows a recognition of some of these problems and an attempt to solve them, but its process uses so much water that its products have too much unnecessary bulk and weight and would not be suitable for incorporation into water-sensitive formulations.

SUMMARY OF THE INVENTION

It has now been found that compositions having a high surfactant content can be obtained by conducting at least the latter part of the reaction of a tert-amine with aqueous hydrogen peroxide to form an amine oxide in the presence of a nonionic surfactant as the sole organic solvent; at least a portion of the nonionic surfactant being a compound corresponding to the formula $Z[OC(Z')HCH_2]_mOH$ in which Z is an alkyl group containing 4–30 carbons, Z' is hydrogen or an alkyl or hydroxyalkyl group containing 1–3 carbons, and m is an integer of 1–100.

It has also been found that the use in the process of a fairly highly concentrated hydrogen peroxide solution and/or the removal of at least a portion of the water from the final reaction mixture can provide a pourable liquid blend of a tert-amine oxide and a solvent consisting essentially of a nonionic surfactant solvent and 0–30% by weight of water, a blend which is suitable for easy incorporation into water-sensitive formulations such as bar soaps and detergent compositions.

DETAILED DESCRIPTION

The amine used in the practice of the invention may be any tert-amine that can be oxidized to a tert-amine oxide with aqueous hydrogen peroxide. Such amines are well known and include a variety of tert-amines having aliphatic, cycloaliphatic, and/or aromatic groups attached to the amino nitrogen. However, they are generally trialkylamines corresponding to the formula RR'R"N wherein R, R', and R" are primary alkyl groups containing 1–30 carbons, preferably such trialkylamines in which R is methyl or ethyl, R' is an alkyl group containing 6–20 carbons, and R" is independently selected from methyl, ethyl, and alkyl groups containing 6–20 carbons.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, N-dodecyldi-2-hydroxyethylamine, N,N-didecyl-2-hydroxyethylamine, and, more preferably, the N-alkyldimethyl-, N-alkyldiethyl-, N-alkyl-N-ethylmethyl-, N,N-dialkylmethyl-, and N,N-dialkylethylamines in which the alkyl groups are hexyl, octyl, decyl, dodecyl, tetradecyl, hexadecyl, octadecyl, and/or eicosyl, as well as mixtures of such amines.

The aqueous hydrogen peroxide which is reacted with the tert-amine may have a concentration of 1–99% by weight but, in a preferred embodiment of the invention, has a concentration or 50–70% by weight. The more dilute solutions are apt to contribute more water to the product than is desired in many instances, but the excess water may be removed from the product after completion of the reaction in those instances.

As in conventional tert-amine/hydrogen peroxide reactions, the amount of hydrogen peroxide employed should be ar least the stoichiometric amount but generally not more than a 15% molar excess; and the reaction is conducted by adding the aqueous hydrogen peroxide to the amine, preferably at a controlled rate and preferably in the presence of carbon dioxide or a chelating agent, such as diethylenetriaminepentaacetic acid or ethylenediaminetetraacetic acid, at a temperature of about 2.0°–100° C., preferably 60°–80° C.; and the reaction temperature is maintained for 1–24 hours.

The process of the invention differs from the conventional processes in that at least the latter part of the reaction is conducted in the presence of a nonionic surfactant as the sole organic solvent. Although the presence of such a solvent in the initial reaction mixture would not prevent the reaction from occurring, it is generally preferred to initiate the reaction in the absence of the organic solvent and then to add it gradually during the reaction so as to maintain the reaction mixture stirrable and/or so as to provide an amine oxide/nonionic surfactant weight ratio of about 0.1–10/1 in the final reaction mixture.

The nonionic surfactant solvent employed in the process contains a compound corresponding to the formula $Z[OC(Z')HCH_2]_mOH$ in which Z is an alkyl group containing 4–30 carbons; Z' is hydrogen or an alkyl or hydroxyalkyl group containing 1–3 carbons, such as methyl, ethyl, propyl, hydroxymethyl, 2-hydroxyethyl, or 3-hydroxypropyl; and m is an integer of 1–100. This compound may comprise only a portion of the nonionic surfactant solvent. However, in a preferred embodiment of the invention, more than 50% by weight of the nonionic surfactant solvent, preferably at least substantially all of it, is composed of this compound.

Nonionic surfactants corresponding to the above formula are well-known compounds which can be prepared by reacting ethylene oxide or an alkyl- or hydroxyalkyl-substituted ethylene oxide with an alkanol containing 4–30 carbons or with a mixture of such alkanols. For use in the present invention, these compounds should be liquids; and the preferred compounds are those in which m is an integer not higher than about 50, preferably 2–15. Also preferred are the compounds prepared from ethylene oxide, i.e., those in which Z' is hydrogen. Particularly good results have been obtained by the use of a mixture of ethoxylates of hexanol and decanol, e.g., such a mixture in which the ethylene oxide unit/alkanol unit mol ratio is an average of three; but good results are also obtained by the use of other compounds corresponding to the above formula, including those formed from one or more other straight- or branched-chain alkanols containing 4–30 carbons, such as butanol, isobutanol, hexanol, octanol, decanol, dodecanol, tetradecanol, pentadecanol, hexadecanol, octadecanol, eicosanol, docosanol, tetracosanol, or triacontanol.

When the surfactant corresponding to the above formula is not the only component of the nonionic surfactant solvent, the remainder may be composed of one or more liquid nonionic surfactants of any type. Exemplary of such other nonionic surfactants (which, like the aforementioned nonionic surfactants, are well known) are sorbitan oleates; sorbitan monolaurate; reaction products of sorbitan fatty acid esters with ethylene oxide; fatty acid (especially lauric) esters of glycols, such as ethylene glycol, diethylene glycol, and 1,2-propanediol; and compounds corresponding to the formulas $T[OC(Z')HCH_2]_mOH$, $ZC(O)[OC(Z')HCH_2]_mOH$, and $ZC(O)NZ'Z''$ wherein T is an alkylphenyl group in which the alkyl group contains 4–30 carbons, Z'' is a hydroxyalkyl group containing 1–3 carbons, and Z, Z', and m have the meanings given above.

Of these optional nonionic surfactants, those apt to be preferred are the alkylphenol ethoxylates, especially those in which the alkyl group contains 8–12 carbons, and the fatty acid amides containing one or two 2-hydroxyethyl groups and prepared from fatty acids such as lauric, linoleic, oleic, coco, stearic, and ricinoleic acids.

After completion of the reaction, the reaction mixture may be cooled to room temperature and, if necessary, then reheated to a fluidizing temperature when the reaction mixture is not fluid and it is desired to be able to pour or pump the reaction product from the vessel in which it was prepared. Alternatively, the reaction product may be poured or pumped from the reaction vessel before the temperature has been reduced to a point at which the product is no longer fluid when it is a product that is apt to gel at lower temperatures.

The amine oxide solution formed by the process contains water because of the use of the aqueous hydrogen peroxide. Since a small amount of water can be tolerated even in water-sensitive formulations in which it might be desired to incorporate the amine oxide, and the solutions containing relatively large amounts of water can be used in formulations which are not water-sensitive, it may not be necessary to remove any of the water in the solution. However, when the solution contains more water than is desired, it is removed from the reaction product by conventional means. The removal of the water may sometimes be accomplished by ordinary distillation, but the relatively low decomposition temperatures of some of the amine oxides makes it preferable to remove the water under reduced pressure to minimize the possibility of decomposing the product. Vacuum stripping is a particularly preferred method of removing at least a portion of the water from the product.

The invention is advantageous in that it provides amine oxide compositions having a high surfactant content that makes them attractive for incorporation into detergents, not only because of their surfactant content but because of their being pourable or pumpable. Moreover, the compositions having low water contents have those advantages as well as an ability to be used in water-sensitive formulations, such as bar soaps and detergent concentrates.

The following example is given to illustrate the invention and is not intended as a limitation thereof.

EXAMPLE

A suitable reaction vessel was charged with 100 g of N-tetradecylidimethylamine and 0.5 g of diethylenetriaminepentaacetic acid. After the mixture was heated to 65° C., 23 g of 70% hydrogen peroxide (a 15% molar excess) was added over a period of five minutes while cooling to prevent the temperature from rising further. The temperature was then raised to 75° C. and held there for approximately seven hours while adding a 3-mol ethoxylate of a hexaonl/decoñal blend as needed to facilitate stirring. By the end of the seven hours, a total of 55 mL of the ethoxylate had been added, and the amine conversion was greater than 95%. The product was a water-white gel which melted to a pumpable fluid near 40° C.

We claim:

1. A pourable liquid blend consisting of a tert-amine oxide; a nonionic surfactant solvent, at least a portion of which is a compound corresponding to the formula $Z[OC(Z')HCH_2]_mOH$ in which Z is an alkyl group containing 4–30 carbons, Z' is hydrogen or an alkyl or hydroxyalkyl group containing 1–3 carbons, and m is an integer of 1–100; and 0–30% of water, based on the weight of the blend.

2. The blend of claim 1 containing not more than about 25% by weight of water.

3. The blend of claim 2 containing not more than about 10% by weight of water.

4. The blend of claim 1 wherein the amine oxide/nonionic surfactant solvent weight ratio is in the range of about 0.1–10/1.

5. The blend of claim 1 wherein the tert-amine oxide is a compound corresponding to the formula RR'R''NO in which R, R', and R'' are primary alkyl groups containing 1–30 carbons.

6. The blend of claim 5 wherein R is methyl or ethyl, R' is an alkyl group containing 6–20 carbons, and R'' is independently selected from the group consisting of methyl, ethyl, and alkyl groups containing 6-20 carbons.

7. The blend of claim 6 wherein R and R" are methyl.

8. The blend of claim 7 wherein the tert-amine oxide is N-tetradecyldimethylamine oxide.

9. The blend of claim 1 wherein the compound corresponding to the formula $Z[OC(Z')HCH_2]_mOH$ is the sole nonionic surfactant solvent.

10. The blend of claim 9 wherein Z' is hydrogen.

11. The blend of claim 10 wherein m is an integer of 2-15.

12. A pourable liquid blend consisting of a tert-amine oxide; a nonionic surfactant solvent which is a mixture of ethoxylates of hexanol and decanol containing 2-15 $-OCH_2CH_2-$ groups per molecule; and 0-30% of water, based on the weight of the blend.

13. The blend of claim 12 wherein the tert-amine oxide is a compound corresponding to the formula RR'R"NO in which R is methyl or ethyl, R' is an alkyl group containing 6-20 carbons, and R" is independently selected from the group consisting of methyl, ethyl, and alkyl groups containing 6-20 carbons.

14. The blend of claim 13 wherein the tert-amine oxide is N-tetradecyldimethylamine oxide..

15. In a process for preparing a tert-amine oxide by reacting a tert-amine corresponding to the formula RR'R"N in which R, R', and R" are primary alkyl groups containing 1-30 carbons with at least a stoichiometric amount of an aqueous hydrogen peroxide solution having a concentration of 50-70% by weight, the improvement which comprises conducting at least the latter part of the reaction in the presence of a nonionic surfactant as the sole organic solvent so as to provide an amine oxide/nonionic surfactant weight ratio of about 0.1-10/1 and a water content not higher than about 30% by weight in the final reaction mixture, at least a portion of the nonionic surfactant being a compound corresponding to the formula $Z[OC(Z')HCH_2]_mOH$ in which Z is an alkyl group containing 4-30 carbons, Z' is hydrogen or an alkyl or hydroxyalkyl group containing 1-3 carbons, and m is an integer of 1-100.

16. The process of claim 15 wherein the tert-amine is reacted at a temperature of 60°-80° C. with at least a stoichiometric amount of an aqueous hydrogen peroxide solution having a concentration of 50-70% by weight in the initial absence of the nonionic surfactant, which is added gradually during the reaction so as to maintain the reaction mixture stirrable.

17. The process of claim 16 wherein the final water content is not higher than about 25% by weight.

18. The process of claim 17 wherein the final water content is not higher than about 10% by weight.

19. The process of claim 15 wherein at least a portion of the water in the mixture resulting from the reaction is removed under reduced pressure.

20. The process of claim 15 wherein R is methyl or ethyl, R' is an alkyl group containing 6-20 carbons, and R" is independently selected from the group consisting of methyl, ethyl, and alkyl groups containing 6-20 carbons.

21. The process of claim 20 wherein R and R" are methyl.

22. The process of claim 15 wherein the compound corresponding to the formula $Z[OC(Z')HCH_2]_mOH$ is the sole nonionic surfactant solvent.

23. The process of claim 22 wherein Z' is hydrogen.

24. The process of claim 23 wherein m is an integer of 2-15.

* * * * *